(12) United States Patent
Miyaura et al.

(10) Patent No.: US 9,149,471 B2
(45) Date of Patent: Oct. 6, 2015

(54) THERAPEUTIC AGENT FOR OSTEOPOROSIS

(71) Applicants: NATIONAL UNIV. CORP. TOKYO UNIV. OF AG. AND TECH, Fuchu-shi (JP); TAIHO PHARMACEUTICAL CO., LTD., Chiyoda-ku (JP)

(72) Inventors: Chisato Miyaura, Fuchu (JP); Masaki Inada, Fuchu (JP); Hidenori Fujita, Tsukuba (JP)

(73) Assignees: NATIONAL UNIVERSITY CORPORATION TOKYO UNIVERSITY OF AGRICULTURE AND TECHNOLOGY, Fuchu-shi (JP); TAIHO PHARMACEUTICAL CO., LTD., Chiyoda-ku (JP)

(*) Notice: Subject to any disclaimer, the term of this patent is extended or adjusted under 35 U.S.C. 154(b) by 41 days.

(21) Appl. No.: 14/041,222

(22) Filed: Sep. 30, 2013

(65) Prior Publication Data

US 2015/0164879 A1  Jun. 18, 2015

(51) Int. Cl.
C07D 215/00 (2006.01)
A61K 31/47 (2006.01)

(52) U.S. Cl.
CPC ...................................... *A61K 31/47* (2013.01)

(58) Field of Classification Search
CPC ... C07D 215/33; C07D 215/38; C07D 215/42
See application file for complete search history.

(56) References Cited

U.S. PATENT DOCUMENTS 8,304,427 B2 * 11/2012 Suda et al. .................... 514/312
2011/0034439 A1   2/2011 Suda et al.

FOREIGN PATENT DOCUMENTS

WO   2009/125597   10/2009
WO   2013/100014    7/2013

OTHER PUBLICATIONS

"Osteoporosis Prevention, Diagnosis and Therapy", JAMA vol. 285, No. 6, pp. 785-794, Feb. 14, 2001.

T.D. Rachner et al.,"Osteoporosis: now and the future", www.thelancet.com, vol. 377, Apr. 9, 2011, pp. 1276-1287.
M. Shiraki et al., Long-Term Treatment of Postmenopausal Osteoporosis with Active Vitamin $D_3$, 1-Alpha-Hydroxycholecalciferol (1α-$OHD_3$) and 1, 24 Dihydroxycholecalciferol (1, 24 $(OH)_2D_3$, Endocrinol, Japan 1985, 32 (2) 305-315.
R. Rizzoli et al., "Adverse Reaction and Drug-Drug Interactions in the Management of Woman with Postmenopausal Osteoporosis", Calcif Tissue Int (2011), 89:91-104.
"Risks and Benefits of Estrogen Plus Progestin in Healthy Postmenopausal Women", JAMA, Jul. 17, 2002—vol. 288, No. 3, pp. 321-333.
M. A. Bolognese, "SERMs and SERMs with estrogen for postmenopausal osteoporosis", Rev. Endocr Metab Disord (2010) 11:253-259.
V Lim et al., "New therapeutic targets for osteoporosis: Beyond denosumab", Maturitas 73 (2012), 269-272.
S. Das et al, "Osteoporosis—a current view of pharmacological prevention and treatment", Drug Design, Development and Therapy, 2013:7, pp. 435-448.
E. Canalis, "New Treatment Modalities in Osteoporosis", Endocrine Practice, vol. 16, No. 5, Sep./Oct. 2010, pp. 855-863.
U.S. Appl. No. 14/369,060, filed Jun. 26, 2014, Fujita, et al.

* cited by examiner

*Primary Examiner* — Heidi Reese
(74) *Attorney, Agent, or Firm* — Oblon, McClelland, Maier & Neustadt, L.L.P.

(57) ABSTRACT

To provide an agent for treating osteoporosis, comprising an acyl thiourea compound represented by the following formula (I) or a salt thereof as an active ingredient:

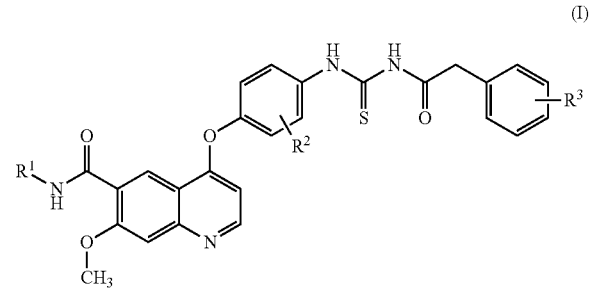

(I)

wherein, $R^1$ represents an optionally substituted $C_{1-6}$ alkyl group; $R^2$ represents a fluorine atom or a chlorine atom; and $R^3$ represents a hydrogen atom, a fluorine atom, or a chlorine atom.

2 Claims, 2 Drawing Sheets

PC-3/Vehicle-administered

PC-3/the subject compound -administered

Normal bone

Control

Normal bone

The subject compound

Zoledronic acid

THERAPEUTIC AGENT FOR OSTEOPOROSIS

FIELD OF THE INVENTION

The present invention relates to an agent for treating osteoporosis containing an acyl thiourea compound or a salt thereof as an active ingredient, and a pharmaceutical composition.

BACKGROUND OF THE INVENTION

At the Consensus Development Conference sponsored by The National Institutes of Health (NIH) in 2000, the definition of osteoporosis was proposed as follows: "A skeletal disorder characterized by compromised bone strength predisposing to an increased risk of fracture." In fact, osteoporosis is perceived as a disease of compromised bone strength due to decreased bone density and deteriorated bone quality (Non Patent Document 1). Osteoporosis is classified into primary osteoporosis and secondary osteoporosis, where the former involves compromised bone density associated with ageing, menopause, and pregnancy, while the latter is caused by some kind of disease as an underlying cause.

Compromised bone density is caused when accelerated bone resorption outpaces bone formation, and is also associated with reduced osteoblast function and associated reduced bone formation (Non Patent Document 2). That is, predominant bone resorption resulting from an imbalance in bone remodeling via bone resorption and bone formation is closely associated with pathology.

At present, in Japan, the number of patients in need of treatment of osteoporosis is assumed to be 12.80 million (2005), including the total of lumbar vertebrae and femoral neck. The number of femoral neck fracture events is rapidly increasing, with the number of patients reaching 148,100 per year. In light of the above, various therapeutic methods and preventive agents are being developed.

Currently, as therapeutic agents for osteoporosis, calcium absorption-promoting drugs, bone formation-promoting drugs, and bone resorption-inhibiting drugs are primarily used. While these therapeutic agents show efficacy, however, serious adverse reactions have been reported. For example, the most frequent adverse reaction to calcium preparations is gastrointestinal disorder. When activated vitamin D3 preparations are concomitantly used, regular blood testing is necessary due to potential hypercalcemia (Non Patent Document 3).

As major adverse reactions to bisphosphonate preparations, for example, gastrointestinal disorder, osteonecrosis of jaw, atypical femur fracture, hypocalcaemia, renal disorder and influenza-like symptoms have been reported (Non Patent Document 4). Moreover, the half-life of bisphosphonate is long, and it may remain in the skeleton for several years even after discontinuation of treatment. Excessive long-term inhibition of bone remodeling may cause unfavorable effects such as brittle bone caused by increased bone mineralization as well as increased microdamage.

Further, for postmenopausal bone mass loss, estrogen preparations, and selective estrogen receptor modulators (SERM), which act on the estrogen receptors on bone more selectively than estrogen preparations, are used. However, for estrogen preparations, not only adverse reactions peculiar to female hormones such as endometrial bleeding, increased vaginal discharge, and breast pain, but also deep vein thromboembolism and increased risk of developing breast cancer and endometrial cancer have been reported (Non Patent Document 5). Further, as to SERM, while adverse reactions affecting the breasts and uterine were successfully inhibited, deep vein thromboembolism, hot flash, and leg cramp are still reported (Non Patent Document 6).

In view of the above, clinical development has recently been taking place for therapeutic agents for osteoporosis aiming at new targets, such as cathepsin K inhibitors, Src kinase inhibitors, and anti-sclerostin antibodies (Non Patent Documents 7, 8, and 9). Nevertheless, the current situation is that no therapeutic drug for osteoporosis which satisfies both excellent efficacy and safety has yet been available.

Meanwhile, acyl thiourea compounds having an aminocarbonyl group at the 6-position and an alkoxy group at the 7-position in the quinolone ring such as 4-[2-fluoro-4-[[[(2-phenylacetyl)amino]thioxomethyl]amino]-phenoxy]-7-methoxy-N-methyl-6-quinolinecarboxamide are known to be an antitumor agent showing a potent inhibitory effect on c-Met and inhibition of VEGF receptors with reduced adverse reactions (Patent Document 1). It is also known that when such a compound is used concomitantly with other antitumor agents, it exhibits an excellent antitumor effect-enhancing action (Patent Document 2).

Nevertheless, this compound is totally unknown to be effective for osteoporosis.

CITATION LIST

Patent Document

[Patent Document 1] WO2009/125597
[Patent Document 2] WO2013/100014

Non Patent Document

[Non Patent Document 1] Osteoporosis prevention, diagnosis, and therapy. JAMA: the journal of the American Medical Association. 2001; 285: 785 to 95.
[Non Patent Document 2] Rachner T D, Khosla S, Hofbauer L C. Osteoporosis: now and the future. Lancet. 2011; 377: 1276 to 87.
[Non Patent Document 3] Shiraki M, Orimo H, Ito H, Akiguchi I, Nakao J, Takahashi R, et al. Long-term treatment of postmenopausal osteoporosis with active vitamin D3, 1-alpha-hydroxycholecalciferol (1 alpha-OHD3) and 1,24 Dihydroxycholecalciferol (1,24(OH)2D3). Endocrinol Jpn. 1985; 32: 305 to 15.
[Non Patent Document 4] Rizzoli R, Reginster J Y, Boonen S, Breart G, Diez-Perez A, Felsenberg D, et al. Adverse reactions and drug-drug interactions in the management of women with postmenopausal osteoporosis. Calcif Tissue Int. 2011; 89: 91 to 104.
[Non Patent Document 5] Rossouw J E, Anderson G L, Prentice R L, LaCroix A Z, Kooperberg C, Stefanick M L, et al. Risks and benefits of estrogen plus progestin in healthy postmenopausal women: principal results From the Women's Health Initiative randomized controlled trial. JAMA: the journal of the American Medical Association. 2002; 288: 321 to 33.
[Non Patent Document 6] Bolognese M A. SERMs and SERMs with estrogen for postmenopausal osteoporosis. Rev Endocr Metab Disord. 2010; 11: 253 to 9.
[Non Patent Document 7] Lim V, Clarke B L. New therapeutic targets for osteoporosis: beyond denosumab. Maturitas. 2012; 73: 269 to 72.
[Non Patent Document 8] Das S, Crockett J C. Osteoporosis—a current view of pharmacological prevention and treatment. Drug Des Devel Ther. 2013; 7: 435 to 48.

[Non Patent Document 9] Canalis E. New treatment modalities in osteoporosis. Endocr Pract. 2010; 16: 855 to 63.

SUMMARY OF THE INVENTION

An object of the present invention is to provide a therapeutic agent and a pharmaceutical composition for osteoporosis, which shows excellent preventive or therapeutic effects on osteoporosis.

The present inventors conducted an intensive study to achieve the aforementioned object. As a result, they have found that an acyl thiourea compound represented by the following formula (I) or a salt thereof inhibits bone resorption by inhibiting differentiation and formation of osteoclasts, while having an inhibitory action on the formation of deformed bone by osteoblasts, thereby being useful for prevention or treatment of osteoporosis.

That is, the present invention provides an agent for treating osteoporosis, comprising an acyl thiourea compound represented by the following formula (I) or a salt thereof as an active ingredient.

The present invention also provides a pharmaceutical composition for treating osteoporosis, comprising an acyl thiourea compound represented by the following formula (I) or a salt thereof and a pharmaceutically acceptable carrier.

The present invention also provides a method for treating osteoporosis, comprising administering a pharmaceutical composition comprising an acyl thiourea compound represented by the following formula (I) or a salt thereof and a pharmaceutically acceptable carrier to a patient in need thereof.

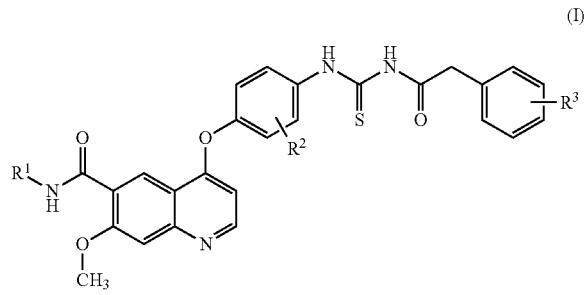

(I)

wherein, $R^1$ represents an optionally substituted $C_{1-6}$ alkyl group, wherein the substituent is any one of a hydroxyl group, a $C_{3-10}$ cycloalkyl group, an optionally substituted $C_{1-6}$ alkoxy group, an optionally substituted $C_{1-6}$ alkylamino group, a $C_{1-6}$ alkanoylamino group, a $C_{1-6}$ alkylsulfonyl group, an optionally substituted $C_{6-14}$ aromatic hydrocarbon group, an optionally substituted saturated or unsaturated heterocyclic group, an optionally substituted $C_{1-6}$ alkylaminocarbonyl group, and an optionally substituted saturated or unsaturated heterocyclic carbonyl group, $R^2$ represents a fluorine atom or a chlorine atom, and $R^3$ represents a hydrogen atom, a fluorine atom, or a chlorine atom.

The compound of the present invention shows a bone resorption-inhibiting effect primarily by inhibiting differentiation and formation of osteoclasts, and further shows an inhibitory effect on the formation of deformed bone by osteoblasts, thereby showing an excellent effect on osteoporosis. Therefore, osteoporosis can be effectively treated by the present invention.

DETAILED DESCRIPTION OF THE INVENTION

Figure 1:
FIG. 1 is a μCT image of the transplantation site of the PC-3 human prostate cancer cell line in the mouse tibia.
Figure 1:
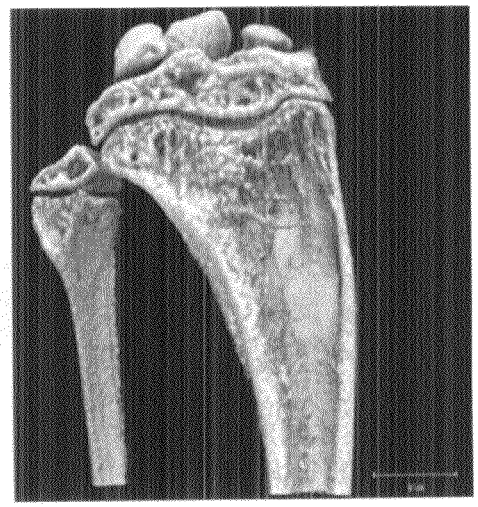
Figure 1:
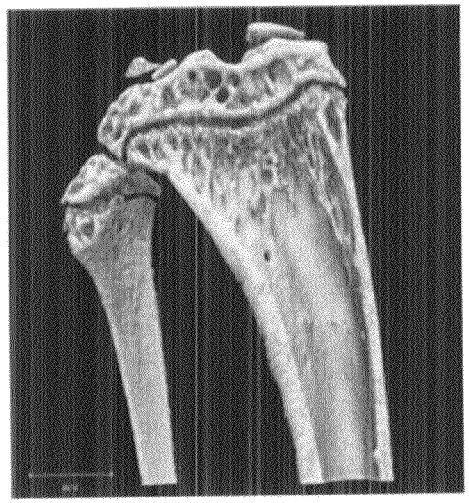

In regard to the acyl thiourea compound represented by the general formula (I) of the present invention (referred to as the "compound of the present invention"), when the compound is referred to as "optionally substituted", it is meant that the compound may have one or two or more "substituents" at chemically possible positions in its structure.

The kind, number, and position of the substituent present in the structure are not particularly limited, and when two or more substituents are present, they may be the same or different. Examples of the "substituent" include a halogen atom, a hydroxyl group, a cyano group, a nitro group, a $C_{1-6}$ alkanoyl group, a $C_{1-6}$ alkyl group, a $C_{3-30}$ cycloalkyl group, a $C_{2-6}$ alkenyl group, a $C_{1-6}$ alkoxy group, an amino group, a $C_{1-6}$ alkylamino group, a $C_{1-6}$ alkanoylamino group, a $C_{1-6}$ alkylaminocarbonyl group, a $C_{1-6}$ alkylsulfonyl group, a $C_{6-14}$ aromatic hydrocarbon group, a saturated or unsaturated heterocyclic group, a saturated or unsaturated heterocyclic carbonyl group, and an oxo group. When the aforementioned substituent is present, the number of the substituent is typically 1 to 3.

In the formula (I), the "$C_{1-6}$ alkyl group" of the "optionally substituted $C_{1-6}$ alkyl group" represented by $R^1$ represents a linear or branched alkyl group having 1 to 6 carbon atoms. Examples of the "$C_{1-6}$ alkyl group" include a methyl group, an ethyl group, an n-propyl group, an isopropyl group, an n-butyl group, a sec-butyl group, a tert-butyl group, an n-pentyl group, an isopentyl group, an n-hexyl group, and an isohexyl group. A $C_{1-4}$ alkyl group is more preferable, and a methyl group, an ethyl group, an n-propyl group, an isopropyl group, an n-butyl group, and a sec-butyl group are particularly preferable.

In the formula (I), the "$C_{3-10}$ cycloalkyl group" indicated as the substituent in the "optionally substituted $C_{1-6}$ alkyl group" of $R^1$ represents a cycloalkyl group having 3 to 10 carbon atoms. Examples of the "$C_{3-10}$ cycloalkyl group" include a cyclopropyl group, a cyclobutyl group, a cyclopentyl group, and a cyclohexyl group. A cyclohexyl group is more preferable.

In the formula (I), the "$C_{1-6}$ alkoxy group" of the "optionally substituted $C_{1-6}$ alkoxy group" indicated as the substituent in the "optionally substituted $C_{1-6}$ alkyl group" of $R^1$ represents a linear or branched alkoxy group having 1 to 6 carbon atoms. Examples of the "$C_{1-6}$ alkoxy group" include a methoxy group, an ethoxy group, an n-propyloxy group, an isopropyloxy group, an n-butyloxy group, a sec-butyloxy group, a tert-butyloxy group, an n-pentyloxy group, and an n-hexyloxy group. A methoxy group, an ethoxy group, and an isopropyloxy group are particularly preferable.

In the formula (I), the "substituent" in the "optionally substituted $C_{1-6}$ alkoxy group" indicated as the substituent in the "optionally substituted $C_{1-6}$ alkyl group" of $R^1$ is preferably a hydroxyl group.

In the formula (I), the "$C_{1-6}$ alkylamino group" of the "optionally substituted $C_{1-6}$ alkylamino group" indicated as the substituent in the "optionally substituted $C_{1-6}$ alkyl group" of $R^1$ represents an amino group monosubstituted or disubstituted with the aforementioned $C_{1-6}$ alkyl group(s). Examples of the "$C_{1-6}$ alkylamino group" include a methylamino group, an ethylamino group, a dimethylamino group, a methylethylamino group, an n-propyl amino group, an isopropylamino group, an n-butylamino group, a sec-butylamino group, a tert-butylamino group, an n-pentylamino group, and an n-hexylamino group. A diethylamino group is more preferable.

In the formula (I), examples of the "$C_{1-6}$ alkanoylamino group" indicated as the substituent in the "optionally substituted $C_{1-6}$ alkyl group" of $R^1$ include a formylamino group, an acetylamino group, a propionylamino group, and a butyrylamino group. An acetylamino group is more preferable.

In the formula (I), "the $C_{1-6}$ alkylsulfonyl group" indicated as the substituent in the "optionally substituted $C_{1-6}$ alkyl group" of $R^1$ represents a sulfonyl group substituted with the aforementioned $C_{1-6}$ alkyl group. A methylsulfonyl group is more preferable.

In the formula (I), the "$C_{6-14}$ aromatic hydrocarbon group" of the "optionally substituted $C_{6-14}$ aromatic hydrocarbon group" indicated as the substituent in the "optionally substituted $C_{1-6}$ alkyl group" of $R^1$ represents an aromatic hydrocarbon group having 6 to 14 carbon atoms. Examples of the "$C_{6-14}$ aromatic hydrocarbon group" include a phenyl group and a naphthyl group. A phenyl group is more preferable.

In the formula (I), the "saturated or unsaturated heterocyclic group" of the "optionally substituted saturated or unsaturated heterocyclic group" indicated as the substituent in the "optionally substituted $C_{1-6}$ alkyl group" of $R^1$ represents a monocyclic or bicyclic saturated or unsaturated heterocyclic group having one or two of oxygen atom, nitrogen atom, and sulfur atom. Examples of the "saturated or unsaturated heterocyclic group" include a pyrrolidinyl group, a piperidinyl group, a piperazinyl group, a morpholino group, a thiomorpholino group, a homopiperidinyl group, a tetrahydrothienyl group, an imidazolyl group, a thienyl group, a furyl group, a pyrrolyl group, an oxazolyl group, an isoxazolyl group, a thiazolyl group, an isothiazolyl group, a pyrazolinyl group, a triazolyl group, a tetrazolyl group, a pyridyl group, a pyrazyl group, a pyrimidinyl group, a pyridazyl group, an indolyl group, an isoindolyl group, an indazolyl group, a methylenedioxyphenyl group, an ethylenedioxyphenyl group, a benzofuranyl group, a dihydrobenzofuranyl group, a benzimidazolyl group, a benzoxazol group, a benzothiazolyl group, a purinyl group, a quinolyl group, an isoquinolyl group, a quinazolinyl group, and a quinoxalyl group. A 5- to 7-membered heterocyclic group having 1 to 4 nitrogen atoms and/or oxygen atoms is more preferable, and a pyrrolidinyl group, a morpholino group, a dioxolan group, a tetrahydropyranyl group, a pyridyl group, and a tetrazolyl group are particularly preferable. The saturated or unsaturated heterocyclic group may further have a substituent, and the substituent is preferably a $C_{1-6}$ alkyl group (particularly, a methyl group) and an oxo group.

In the formula (I), the "$C_{1-6}$ alkylaminocarbonyl group" of the "optionally substituted $C_{1-6}$ alkylaminocarbonyl group" indicated as the substituent in the "optionally substituted $C_{1-6}$ alkyl group" of $R^1$ represents a carbonyl group having the aforementioned $C_{1-6}$ alkylamino group, and an ethylaminocarbonyl group, a dimethylamino group, and a methylbutylamino group are more preferable. The $C_{1-6}$ alkylaminocarbonyl group may further have a substituent, and the substituent is preferably a hydroxyl group and a $C_{1-6}$ alkoxy group (particularly, a methoxy group).

In the formula (I), the "saturated or unsaturated heterocyclic carbonyl group" of the "optionally substituted saturated or unsaturated heterocyclic group carbonyl group" indicated as the substituent in the "optionally substituted $C_{1-6}$ alkyl group" of $R^1$ represents a carbonyl group having the aforementioned saturated or unsaturated heterocyclic group. A 5- to 7-membered saturated heterocyclic carbonyl group having 1 to 2 nitrogen atoms and/or oxygen atoms is more preferable, and a pyrrolidinylcarbonyl group and a morpholinocarbonyl group are particularly preferable. The saturated or unsaturated heterocyclic carbonyl group may further have a substituent, and the substituent is preferably a halogen atom (particularly, a fluorine atom) and a $C_{1-6}$ alkyl group (particularly, a methyl group) optionally having a hydroxyl group.

The $C_{1-6}$ alkyl group of the optionally substituted $C_{1-6}$ alkyl group represented by $R^1$ is preferably a methyl group, an ethyl group, an n-propyl group, an isopropyl group, an n-butyl group, or a sec-butyl group, and the substituent in the alkyl group is preferably a hydroxyl group, a cyclohexyl group, a methoxy group, an ethoxy group, an isopropyloxy group, a diethylamino group, an acetylamino group, a methylsulfonyl group, a phenyl group, a pyrrolidinyl group, a morpholino group, a dioxolan group, a tetrahydropyranyl group, a pyridyl group, a triazolyl group, an ethylaminocarbonyl group, a dimethylaminocarbonyl group, a methylbutylaminocarbonyl group, a pyrrolidinylcarbonyl group, or a morpholinocarbonyl group. The alkoxy group may further have a hydroxyl group as a substituent, and the heterocyclic group may further have a methyl group or an oxo group as a substituent, and the alkylaminocarbonyl group may further have a hydroxyl group or a methoxy group as a substituent, and the heterocyclic carbonyl group may further have a methyl group optionally having a fluorine atom and a hydroxyl group as a substituent.

The $C_{1-6}$ alkyl group of the optionally substituted $C_{1-6}$ alkyl group represented by $R^1$ is preferably a methyl group, an ethyl group, an n-propyl group, an isopropyl group, an n-butyl group, or a sec-butyl group, and the substituent in the alkyl group is preferably a hydroxyl group, a methoxy group, or a morpholino group.

$R^1$ is more preferably a methyl group, a methoxyethyl group, a morpholinoethyl group, a morpholinocarbonylmethyl group, a 2-hydroxy-n-butyl group, a 2-hydroxy-2-methyl-n-propyl group, and a 1-hydroxy-n-butan-2-yl group, and when $R^1$ is a 1-hydroxy-n-butan-2-yl group, the S form is preferable.

The position of substitution of $R^2$ is preferably the 2- or 3-position, particularly preferably the 2-position. Also, $R^2$ is preferably a fluorine atom or a chlorine atom, and more preferably a fluorine atom.

The position of substitution of $R^3$ is preferably the 2- or 4-position. Also, $R^3$ is more preferably a hydrogen atom or a fluorine atom.

Among the compounds of the present invention, one in which $R^1$ is an optionally substituted methyl group, ethyl group, n-propyl group, isopropyl group, n-butyl group, or sec-butyl group, wherein the substituent in $R^1$ is absent or is a hydroxyl group, a methoxy group, or a morpholino group, $R^2$ is a fluorine atom, and $R^3$ is a hydrogen atom or a fluorine atom is preferable.

Further, preferable specific examples of the compound of the present invention include the following compounds.

(1) 4-(2-fluoro-4-(3-(2-phenylacetyl)thioureido)phenoxy)-7-methoxy-N-methylquinoline-6-carboxamide
(2) 4-(2-fluoro-4-(3-(2-phenylacetyl)thioureido)phenoxy)-7-methoxy-N-(2-morpholinoethyl)quinoline-6-carboxamide
(3) (S)-4-(2-fluoro-4-(3-(2-(4-fluorophenyl)acetyl)thioureido)phenoxy)-N-(1-hydroxybutan-2-yl)-7-methoxyquinoline-6-carboxamide Among those shown above, 4-(2-fluoro-4-(3-(2-phenylacetyl)thioureido)phenoxy)-7-methoxy-N-methylquinoline-6-carboxamide [alternative name: (4-[2-fluoro-4-[[[(2-phenylacetyl)amino]thioxomethyl]amino]-phenoxy]-7- methoxy-N-methyl-6-quinolinecarboxamide)] represented by the following formula (1A) is more preferable.

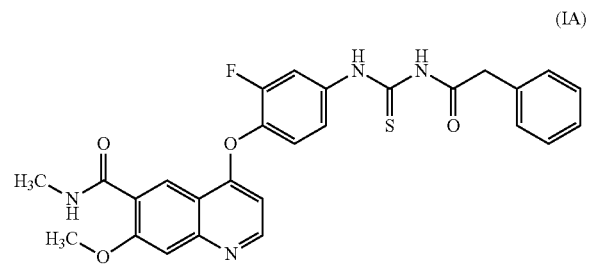 [SMILES: CNC(=O)c1cc2c(Oc3ccc(NC(=S)NC(=O)Cc4ccccc4)cc3F)ccnc2cc1OC]

(IA)

A salt of the compound of the present invention may be a pharmaceutically acceptable salt, and examples thereof include an acid addition salt formed with an inorganic acid such as hydrochloric acid, hydrobromic acid, hydriodic acid, sulfuric acid, nitric acid, and phosphoric acid, an acid addition salt formed with an organic acid such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, p-toluenesulfonic acid, and glutamic acid, a salt formed with an inorganic base such as sodium, potassium, magnesium, calcium, and aluminum, a salt formed with an organic base such as methylamine, ethylamine, meglumine, and ethanolamine, a salt formed with a basic amino acid such as lysine, arginine, and ornithine, and an ammonium salt.

Among those mentioned above, a salt formed with an organic acid is preferable, and a methanesulfonic acid salt is more preferable, and a monomethanesulfonic acid salt is even more preferable.

Further, the compound of the present invention encompasses optical isomers as well as hydrates, various solvates, and crystal polymorphs.

The compound of the present invention may be in the form of a pharmacologically acceptable prodrug. The pharmacologically acceptable prodrug may be any as long as it is converted into the general formula (I) under physiological conditions in vivo, which are, for example, hydrolysis by gastric juice or enzymes, oxidation, and reduction reaction. Examples of the pharmacologically acceptable prodrug include an ester-type compound such as methyl ester, ethyl ester, propyl ester, phenyl ester, carboxyoxymethyl ester, and ethoxycarbonyl ester, in which the carboxyl group is modified. Representative compounds which form these prodrugs include the compounds which are converted into the compound (I) under such physiological conditions as those described in "Iyakuhin no kaihatsu (literal translation: Development of Pharmaceutical Products")", Hirokawa Shoten Co., 1990, Vol. 7, pp. 163 to 198.

The compound of the present invention is a publicly known compound, and may be produced in accordance with, for example, the method described in International Publication No. WO2009/125597 (the aforementioned Patent Document 1).

As will be demonstrated in Examples to be described later, the compound of the present invention maintains a normal level of bone mass by inhibiting accelerated bone destruction and formation of abnormal brittle bone in the mouse model of intratibial transplantation of cancer cell line (Test Examples 1 and 2). Further, the compound of the present invention shows an inhibitory effect on bone resorption also in the ovariectomized animal model, which is known as a typical model of osteoporosis.

Accordingly, the compound of the present invention or a salt thereof is useful as a drug showing an excellent preventive or therapeutic effect on osteoporosis in patients in need thereof.

In regard to the therapeutic agent for osteoporosis and pharmaceutical composition for treating osteoporosis according to the present invention, "treatment" means prevention and treatment of a disease, alleviation of symptoms, and maintenance therapy for prevention of recurrence.

In the present specification, "osteoporosis" refers to primary as well as secondary bone disease characterized by increased risk of bone fracture due to compromised bone strength caused by bone mass loss and degraded bone quality. Examples of osteoporosis which can be treated by the therapeutic agent for osteoporosis and pharmaceutical composition for treating osteoporosis according to the present invention include postmenopausal osteoporosis, male osteoporosis, idiopathic osteoporosis (such as post-pregnancy osteoporosis), and osteogenesis imperfecta.

The compound of the present invention or a salt thereof may be prepared as either oral or parenteral dosage form, and it may be produced as a pharmaceutical composition using a pharmaceutically acceptable carrier by a publicly known method. The formulation of the pharmaceutical composition is not particularly limited, and examples thereof may include an oral preparation such as a tablet, a coated tablet, a pill, a powder, a granule, a capsule, a liquid preparation, a suspension, and an emulsion; and a parenteral preparation such as an injection and a suppository.

When the pharmaceutical composition is formulated into a tablet, as a carrier, for example, an excipient such as lactose, sucrose, sodium chloride, glucose, urea, starch, calcium carbonate, kaolin, crystalline cellulose, and silicic acid; a binder such as water, ethanol, propanol, corn starch, a simple syrup, a glucose solution, a starch solution, a gelatin solution, carboxymethylcellulose, shellac, methylcellulose, hydroxypropylcellulose, hydroxypropylmethylcellulose, potassium phosphate, and polyvinylpyrrolidone; a disintegrator such as dry starch, sodium alginate, agar powder, laminaran powder, sodium bicarbonate, calcium carbonate, polyoxyethylene sorbitan fatty acid esters, sodium lauryl sulfate, stearyl monoglyceride, and lactose; a disintegration inhibitor such as sucrose, stearic acid, cocoa butter, and hydrogenated oil; an absorption promoter such as a quaternary ammonium salt and sodium lauryl sulfate; a humectant such as glycerin and starch; an adsorbent such as starch, lactose, kaolin, bentonite, and colloidal silicic acid; and a lubricant such as purified talc, a stearic acid salt, boric acid powder, and polyethylene glycol may be used. Further, a tablet may be provided as a conventionally coated tablet as needed such as a sugar coated tablet, a gelatin coated tablet, an enteric coated tablet, a film coated tablet, a double-layered tablet, and a multi-layered tablet.

When the pharmaceutical composition is formulated into a pill, as a carrier, for example, an excipient such as glucose, lactose, starch, cocoa butter, hydrogenated vegetable oil, kaolin, and talc; a binder such as gum arabic powder, tragacanth powder, gelatin, and ethanol; and a disintegrator such as laminaran and agar can be used. Capsules may be prepared by mixing the compound of the present invention or a salt thereof with various carriers exemplified above and filling the resulting mixture to, for example, hard gelatin capsules, soft capsules with in accordance with a conventional method.

When the pharmaceutical composition is provided as an oral liquid preparation, for example, an orally administered liquid preparation, a syrup, an elixir may be produced by a conventional method using, for example, a taste and odor masking agent, a buffer, a stabilizer. In this case, examples of the taste and odor masking agent include sucrose, orange peel, citric acid, and tartaric acid, and examples of the buffer include sodium citrate, and examples of the stabilizer include tragacanth, gum arabic, and gelatin.

When the pharmaceutical composition is formulated into a suppository, as a carrier, for example, polyethylene glycol, cocoa butter, higher alcohol, esters of higher alcohol, gelatin, and semi-synthesized glyceride may be used.

When the pharmaceutical composition is provided as an injection, a liquid preparation, an emulsion, and a suspension are preferably sterilized and isotonic with blood. When the pharmaceutical composition is formulated into these dosage forms, as a diluent, for example, water, an aqueous solution of lactic acid, ethyl alcohol, propylene glycol, macrogol, ethoxylated isostearyl alcohol, polyoxyethylenated isostearyl alcohol, and polyoxyethylene sorbitan fatty acid esters may be used.

Also, in this case, sodium chloride, glucose, or glycerin may be contained in the pharmaceutical preparation in an amount sufficient to prepare an isotonic solution, and further, for example, a common solubilizing aid, a buffer, a soothing agent may also be added. Further, for example, a colorant, a preservative, a fragrance, a flavoring agent, a sweetener as well as other pharmaceutical products may also be blended in each of the aforementioned preparations as needed.

A method for administering the therapeutic agent for osteoporosis and pharmaceutical composition for treating osteoporosis according to the present invention is appropriately determined according to, for example, various dosage forms, the age, sex, and other conditions of a patient in need thereof, the severity of the symptoms of a patient in need thereof. For example, a tablet, a pill, a powder, a granule, a capsule, a liquid preparation, a suspension, and an emulsion are orally administered. An injection is intravenously administered alone or as a mixture with a common replenisher such as glucose and amino acid, and further, when necessary, an injection is administered intraarterially, intramuscularly, intradermally, subcutaneously, or intraperitoneally alone. A suppository is rectally administered.

The amount of the compound of the present invention or a salt thereof blended in each of the aforementioned unit dosage forms varies according to, for example, the symptoms of a patient in need of the compound of the present invention or a salt thereof, the dosage form of the compound of the present invention or a salt thereof. However, generally, the amount per unit dosage form is desirably approximately 0.005 to 1,000 mg in an oral preparation, approximately 0.001 to 500 mg in an injection, and approximately 0.01 to 1,000 mg in a suppository. Also, although the daily dose of a drug in the aforementioned dosage form varies according to, for example, the symptoms, body weight, age, sex of a patient in need thereof and thus cannot be generalized, normally, the adult daily dose is approximately 0.005 to 5,000 mg, preferably 0.01 to 1,000 mg. The above dose is preferably administered once daily or approximately two to four times daily in divided doses.

Hereinbelow, the present invention will be described further in detail with reference to Examples and Test Examples; however, the present invention is not limited thereto.

EXAMPLES

Production Example 1

Synthesis of 4-[2-fluoro-4-[[[(2-phenylacetyl)amino]thioxomethyl]amino]-phenoxy]-7-methoxy-N-methyl-6-quinolinecarboxamide (Compound IA)

The title compound IA was synthesized in accordance with the description of Example 6 in International Publication No. WO2009/125597 (the aforementioned Patent Document 1).

Test Example 1

Inhibitory Effect on the Abnormal Bone Formation and Bone Resorption in the Mouse Model Intratibially Transplanted with a PC-3 Human Prostate Cancer Cell Line The PC-3 human prostate cancer cell line was transplanted in the mouse tibia at $2\times10^6$ cells/15 µL. On the following day of transplantation, the mice were grouped so that the average body weight of the mice in each group was equal, and the compound IA was administered orally at 200 mg/kg/day every day for 10 days. On Day 11 after transplantation, the graft site was imaged by µCT and bone lesions were evaluated.

As shown in FIG. 1, in the mouse transplanted with the PC-3 human prostate cancer cell line in the tibia, abnormal bone formation was noted in the bone at the graft site. The compound of the present invention evidently inhibited the abnormal bone formation.

The above results showed that the compound IA maintained a normal level of bone mass by inhibiting accelerated metabolic bone destruction and formation of abnormal brittle bone in the mouse model intratibially transplanted with human prostate cancer cells without causing death or reducing body weight.

Test Example 2

Inhibitory Effect on the Abnormal Bone Formation and Bone Resorption in the Mouse Model Intratibially Transplanted an A549-Luc-BM1 Human Lung Cancer Cell Line The A549 human lung cancer cell line in which the luciferase gene was transfected was transplanted in the left ventricle of nude mice, whereby the A549-luc-BM1 lung cancer cell line, which selectively metastasizes to and proliferates in the bone, was established. The cells thus obtained were transplanted in the mouse tibia at $2\times10^6$ cells/15 µL. On Day 7 after transplantation, the luciferase activity in the graft site was measured by an in-vivo imaging system. Subsequently, the mice were grouped so that the average luciferase activity of each group was equal, and the compound IA was administered orally at 200 mg/kg/day every day for 28 days. The treatment control group received subcutaneous administration of zoledronic acid, which is the third-generation bisphosphonate preparation, at 0.2 mg/kg/day twice a week. For the evaluation of bone lesions, the graft site was imaged by µCT on Day 36 after transplantation.

Figure 2:
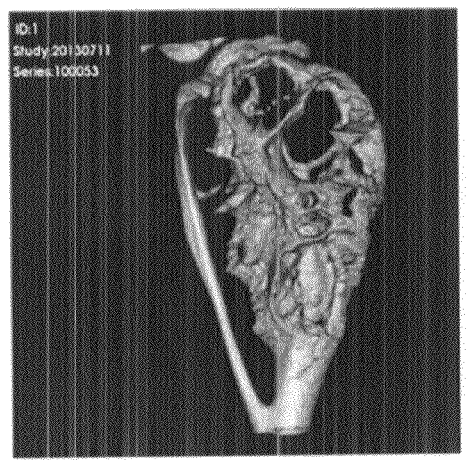
FIG. 2 is a μCT image of the transplantation site of the A549-luc-BM1 human lung cancer cell line in the mouse tibia.
Figure 2:
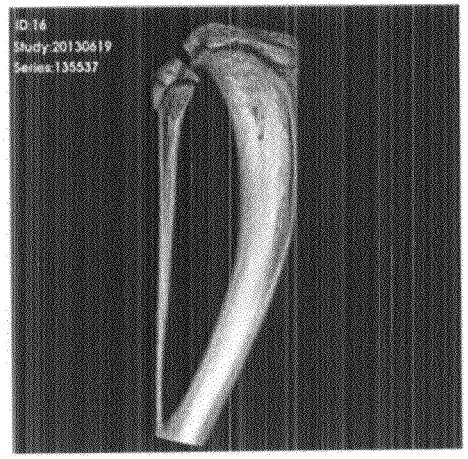
Figure 2:
Figure 2:
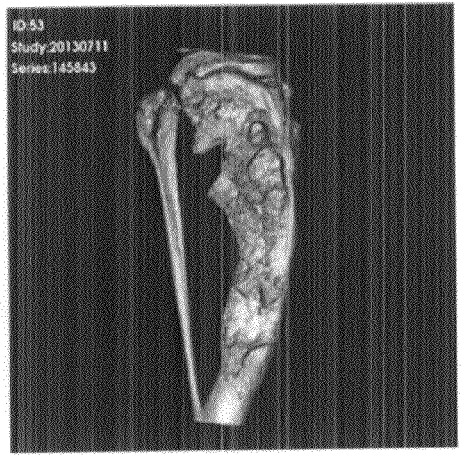

The evaluation of bone lesions in the graft site in the mouse transplanted with the A549-luc-BM1 human lung cancer cell line in the tibia is shown in FIG. 2. On Day 36 after transplantation, the tibia was greatly deformed due to abnormal bone destruction and deformation in the control. Meanwhile, the compound of the present invention remarkably inhibited bone destruction and deformation whereby morphology close to normal bone was maintained. Also, although bone destruction was inhibited by zoledronic acid, which is a control treatment drug, abnormal bone formation was observed, resulting in malformed bone.

The above results showed that the compound IA had a better inhibitory effect on abnormal bone metabolism (bone resorption and bone formation) than zoledronic acid, thereby being useful as an agent for treating osteoporosis.

What is claimed is:

1. A method for treating osteoporosis, the method comprising administering a pharmaceutical composition comprising an acyl thiourea compound represented by formula (I) or a salt thereof and a pharmaceutically acceptable carrier to a patient in need thereof:

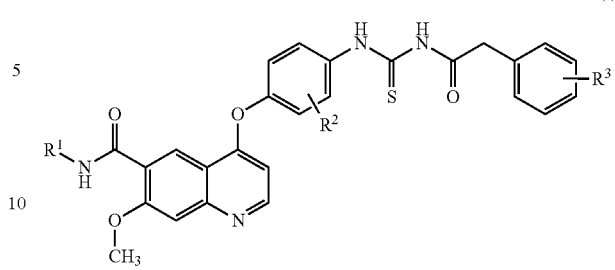

wherein, $R^1$ represents an optionally substituted $C_{1-6}$ alkyl group, wherein a substituent is any one of a hydroxyl group, a $C_{3-10}$ cycloalkyl group, an optionally substituted $C_{1-6}$ alkoxy group, an optionally substituted $C_{1-6}$ alkylamino group, a $C_{1-6}$ alkanoylamino group, a $C_{1-6}$ alkylsulfonyl group, an optionally substituted $C_{6-14}$ aromatic hydrocarbon group, an optionally substituted saturated or unsaturated heterocyclic group, an optionally substituted $C_{1-6}$ alkylaminocarbonyl group, and an optionally substituted saturated or unsaturated heterocyclic carbonyl group;

$R^2$ represents a fluorine atom or a chlorine atom; and $R^3$ represents a hydrogen atom, a fluorine atom, or a chlorine atom.

2. The method according to claim 1, wherein the acyl thiourea compound is 4-[2-fluoro-4-[[[(2-phenylacety)amino]thioxomethyl]amino]-phenoxy]-7-methoxy-N-methyl-6-quinolinecarboxamide monomethanesulfonate.

* * * * *